United States Patent [19]
Flock et al.

[11] Patent Number: 5,897,494
[45] Date of Patent: Apr. 27, 1999

[54] VIBROMETER

[75] Inventors: Stephen T. Flock, Little Rock; Scott Ferguson, Vilonia; John L. Dornhoffer, Roland, all of Ark.

[73] Assignee: The Board of Trustees of the University of Arkansas, Little Rock, Ark.

[21] Appl. No.: 08/792,249

[22] Filed: Jan. 31, 1997

[51] Int. Cl.⁶ .................................................... A61B 5/05
[52] U.S. Cl. ...................... 600/407; 600/473; 600/559; 600/587
[58] Field of Search .................... 600/407, 473, 600/476, 437, 438, 453, 552, 587; 356/351; 73/657

[56] References Cited

U.S. PATENT DOCUMENTS

| | | | |
|---|---|---|---|
| 4,185,503 | 1/1980 | Saito | 73/653 |
| 4,339,954 | 7/1982 | Anson et al. | 600/595 |
| 4,768,381 | 9/1988 | Sugimoto | 73/657 |
| 4,834,111 | 5/1989 | Khanna et al. | 600/587 |
| 5,394,233 | 2/1995 | Wang | 356/5.01 |

OTHER PUBLICATIONS

Keilson, et al., "Spontaneous Cellular Vibrations in the Guinea–Pig Cochlea" (Acta Otolarynol, 1993, pp. 591–597.
Eiber, "Mechanical Modelling of the Human Middle Ear", Abstracts of the Second European Conference on Engineering and Medicine, 1993.
"Laser Vibrometer", Polytec, undated.
"Polytec Scanning Vibrometer," Polytec, undated.
Gyo, et al, "Measurement of the Ossicular Vibration Ration in Human Temporal Bones by Use of a Video Measuring System," Acta Otolaryngol.
(Stockholm) 103, 87–95, 1987.
VonUnge, et al, "Displacement of the Gerbil Tympanic Membrane Under Static Pressure Variations Measured with a Real–time Differential Moire Interometer," Hearing Res. 70, 229–242, 1993.

Kossl, et al., "Basilar Membrane Resonance in the Cochlea of the Mustached Bat," Proc. Natl. Acad. Sci. USA, 92, 276–279 (1995).
Decreamer, et al., "A Method for Determining Three–Dimensional Fibration in the Ear," Hearing Res. 77, 19–37 (1994).
Goode, et al., "Measurement of Umbo Vibration in Human Subjects—Method and Possible Clinical Applications," Am. J. Otol. 14, 247–251 (1993).
"Combined fibre optic laser velocimeter and electronic speckle pattern interferometer with a common reference beam," Meas. Sci. Tech. 4,578–582, 1993.
"Laser interferometer microscopic for the measurement of nanometer vibrational displacements of a light scattering microscopic object," J. Acoustic Soc. Am. 83, 1667–1674, 1988.
"Opto–electronic system for displacement and vibration measurement," Rev. Sci. Instrum. 58, 1678–1681, 1987.

(List continued on next page.)

*Primary Examiner*—Brian Casler
*Attorney, Agent, or Firm*—Ray F. Cox, Jr.

[57] ABSTRACT

A vibrometer which detects the variation of the speckle interference pattern of reflected waves as a means of determining the amplitude and frequency of vibrations of structures, including small anatomical structures. A wave source such as a laser delivers wave radiation to the object whose vibration is to be measured. The diffuse reflectance from the textural surface of the object reflects the incident wave radiation as a speckle interference pattern which is detected by a detector, such as a photodetector. The wave radiation source may be a continuous-wave laser, and the photodetector detector may be a phototransistor connected to a wide-bandwidth amplifier. As the object vibrates, the speckle interference pattern moves. The variation in the speckle interference pattern across the detector carries amplitude and frequency information regarding the vibrating object.

26 Claims, 1 Drawing Sheet

OTHER PUBLICATIONS

"Simple method of measuring vibration amplitudes at better than nanometer sensitivity," Rev. Sci. Instrum. 59, 2626–2628, 1988.

"Minimum detectable phase shift in spectrum–analysis techniques of optical interferometric vibration detection," Applied Optics 5997–6002, Oct. 1992.

"Double–pulse electronic speckle interferometry for vibraton analysis," Applied Optics, 7857–7863, Dec. 1994.

"Four–beam two–focus differential laser velocimetry system", Aug. 1992.

"Two–frequency displacement measurement interferometer based on a double–heterodyne technique," Rev. Sci. Instrum., 254–255, Jan. 1991.

"Measuring small vibrations with interferomtery," Am. J. Phys. 58, 919–922, Oct. 1990.

"Non–contact surface vibration analysis using a monomode fibre optic interferometer incorporating an opean air path," The Institute of Physics, 1985.

"The effect of tympanic membrane performation size on umbo velocity in the rat," Laryngoscope, 71–76, Jan. 1996.

Radio Electronics, vol. 58(10), 40–44, 1987.

"Advances in the development of the interferometic otoscope," Laryngoscope, 263–267, Mar. 1996.

"Sound pressure gain produced by the human middle ear," Otolarngology–Head and Neck Surgery, 113(4), 349–355, Oct. 1995.

"On the acoustic coupling of the eardrum," 207–208, undated.

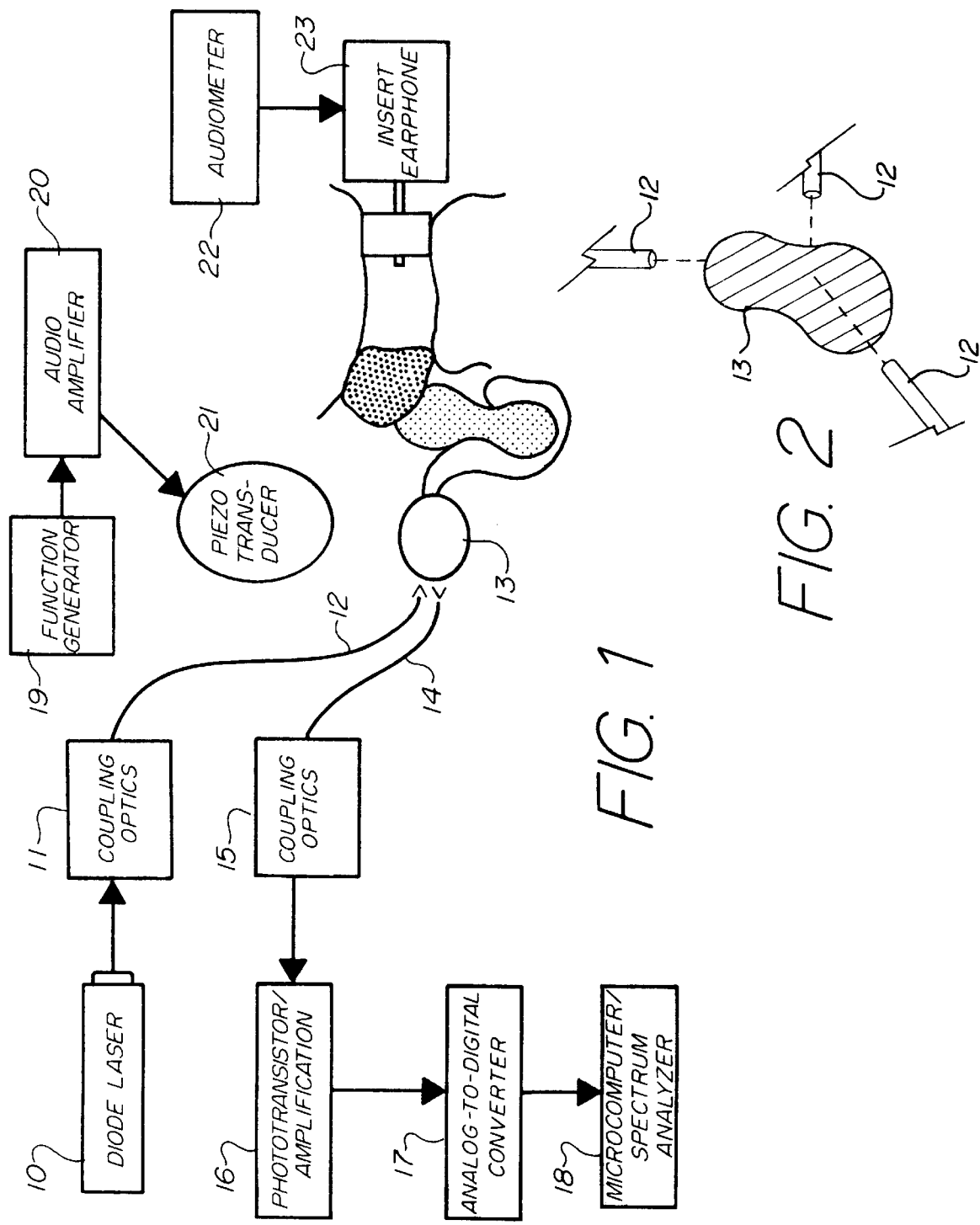

VIBROMETER

BACKGROUND OF THE INVENTION

The present invention relates to measurement of vibrations of objects based on reflectance of speckle interference patterns from incident waves, and in particular embodiments, to optically based in vivo measurement of the small amplitude vibrations of the bones of the middle ear.

Measurement of the displacement or velocity of the bones in the middle ear is one way to objectively characterize the function of the tympanic membrane and ossicular chain, as well as the stapedial footplate. This measurement has been done using a variety of physical measurements. Gyo et al., "Measurement of the Ossicular Vibration Ratio in Human Temporal Bones by Use of a Video Measuring System", Acta Otolaryngol (Stockh) 103, 87–95, 1987, disclose a video measuring system to determine the vibration of the ossicles in a human temporal bone resulting from a sound stimulus. While this procedure is able to measure displacement amplitudes down to 0.3 µm, it suffers from being extremely expensive to implement and requires the placement on the ossicular chain of a bead that can be imaged.

Von Unge et al., "Displacement of the Gerbil Tympanic Membrane Under Static Pressure Variations Measured With a Real-time Differential Moiré Interferometer", Hearing Res. 70, 229–242, 1993, disclose a real-time differential moiré interferometer to measure tympanic membrane displacement in a gerbil model. This method allows one to image the actual shape of the tympanic membrane under different pressure conditions, but it again is expensive and very difficult to implement because of the requirement of real-time image analysis for extraction of quantitative data. Others have used heterodyne Michelson interferometry to extract sub-micron movements; e.g., Kossl et al., "Basilar Membrane Resonance in the Cochlea of the Mustached Bat", Proc. Natl. Acad. Sci. USA, 92, 276–279, 1995; and Decraemer et al., "A Method for Determining Three-Dimensional Vibration in the Ear", Hearing Res. 77, 19–37, 1994. However, it is unlikely such a method could be economically used in vivo due to variations in the index-of-refraction of the atmosphere in each arm of the interferometer which can introduce spurious readings. Also, analysis of the output from an interferometer requires complex calculation steps to obtain movement information from fringe count.

Finally, Goode et al., "Measurement of Umbo Vibration in Human Subjects-Method and Possible Clinical Applications", Am.J.Otol. 14,247–251, 1993, disclose an extremely sensitive technique to measure umbo vibration in vivo using a laser doppler vibrometer.

This instrument has produced some very interesting measurements, such as the peak-to-peak displacement of the umbo and stapes footplate of 0.002 to 0.7 µm when 105 dB SPL pure tone impinges on the TM. More recently, this instrument (Polytec PI Inc., CA) has been used to measure umbo velocity in the rat. While this instrument has the benefits of providing a (potentially) non-contact measurement, and a wide frequency and amplitude range with high spatial resolution, its cost is prohibitive in today's medical environment ($30,000–$40,000) and in practice, it and other instruments like it, require affixing a small reflective object on the object of interest, which has the further disadvantage of affecting the vibrational characteristics of the object being measured.

U.S. Pat. No. 5,394,233 discusses several variations on the basic doppler approach which dominates laser vibrometer technology. Some vibrometers exploit a difference between an incident and reflected laser beam by relying on mirrors or corner reflectors attached to the vibrating object. Examples of devices based on this concept are disclosed in U.S. Pat. Nos. 4,768,381 and 4,185,503.

It is desirable to be able to monitor the success of middle ear surgery such as when prostheses are implanted. Measurement of the reaction of the implanted prostheses to sound indicates the success of the procedure by objective measurement without closure of the wound and without depending on subjective reactions of the patient. Such a device could also be employed to monitor hair cell motion in the cochlea or tympanic membrane displacement. It is also highly desirable that such a device be suitable for use in vivo.

It has not been recognized that the surface of the bones of the middle ear and prostheses, provides sufficient reflectivity, both diffuse and specular (mirror-like), to allow direct optically based vibration measurements based on detection of the reflected beam. The prior art has relied on specular reflectance and, as mentioned above, has resorted to expedients such as the attachment of a mirror-like object on the object of interest in order to obtain the necessary degree of reflectance.

In order to overcome the problems and limitations of the prior art, it is therefore desirable to develop an inexpensive ergonometrically designed instrument to objectively and scientifically measure the vibrational amplitude transmitted by vibrating objects, and in particular, the bones in the middle ear. Such an instrument would, for example, allow a surgeon to objectively test the quality of a bone prosthesis surgery in vivo immediately after surgery, but before closing the operative field. The benefits of such an instrument include providing an objective measurement of acoustic transmission and precluding the need for immediate corrective surgery.

An instrument suitable for measuring the acoustic signal produced by the vibration of bones and membranes should exhibit these features: it should be inexpensive compared to the prior art, it should be portable, it is desirable that it run on rechargeable batteries, it should be usable in conjunction with millimeter-sized endoscopes, it should be hand-held and easy to use, it should be visually directed to interrogate millimeter-sized objects, it should not be affected by ambient and unrelated acoustic signals.

SUMMARY OF THE INVENTION

Infection or cholesteatoma growth in the middle ear can adversely affect the ossicular chain and result in profound hearing loss. As a result, it is sometimes necessary to replace one or all of the ossicles with a prosthesis in order to save the patient's hearing function. The success of the procedure depends not only on the surgeon's skill, but also on the vibrational characteristics of the prostheses.

It is also desirable to have the capability of inexpensively measuring vibrations in various non-medical situations. For example, failures in rotating machinery are often related to vibration modes.

The devices used to date to measure vibrations involve interferometry, laser doppler velocimetry, speckle pattern interferometry, phase sensitive detection, and holography and the Mossbauer effect. Many, if not all of these techniques have been used in physiologic measurements.

When prostheses are implanted in the middle ear, for example, it is necessary to be able to test the vibration characteristics of bones in the middle ear prior to completing the operation and waking the patient. The prior art devices to accomplish this function rely primarily on laser doppler technology, which is complex and costly.

Measurements of extremely small vibrational amplitudes, velocities, or surface profiles often make use of interferometry. The smallest vibrational displacements that can be measured interferometrically are on the order of $10^{-6}$ nm, but due to limitations in the reflectance of some materials, such measurements are usually limited to about 0.01 nm.

Speckle pattern interferometry makes use of either changing contrast in the overall speckle pattern, or fringe formation in the pattern, and thus is different from our technique which makes use of the movement of speckles. Further the present invention does not use interferometry and thus does not require a reference beam.

The present invention detects the motion of the speckle interference pattern of reflected incident waves as a means of determining the amplitude and frequency of vibrations of objects, including small anatomical structures. The speckle interference pattern is a natural consequence of the reflection of light, or any propagating electromagnetic wave or density wave, such as a pressure or acoustic wave in a solid, liquid or gas, from a surface with irregularities. The effect is most noticeable when the impinging wave is coherent, but the phenomenon is not limited to coherent waves. All waves are coherent to some degree.

The present invention is suitable for use in vivo since it can be used in conjunction with thin optical fibers which can be inserted via thin endoscopes. Other medical uses for the present invention include monitoring hair cell motion in the cochlea or tympanic membrane displacement. The present invention may be used without optical fibers in both medical and non-medical applications. In one embodiment, the present invention is suitable for measuring the vibrational characteristics of the oval window, which is the terminal component of the ossicular chain in the middle ear.

This vibrometer of the present invention uses the movement of the speckle pattern produced by the diffuse reflectance of light or other waves off bone or other reflective surfaces, to obtain vibrational information. Coherent laser light is suitable, although the present invention is not so limited. A highly reflective surface on the object being measured is not necessary to the practice of the present invention. Most objects of interest are sufficiently reflective. Since all objects have some degree of surface roughness, reflected waves from surfaces always demonstrate interference in the reflected beam and therefore produce a speckle interference pattern. Vibration of an object being illuminated causes the speckle interference pattern to move, from which movement of the object of interest may be detected. The detected variation in the speckle interference pattern due to the movement of the vibrating surface carries information on the amplitude and frequency of the vibrations of the object being illuminated.

Measurements on a vibrating piezoelectric membrane using a laser based device have shown that a laser vibrometer form of the present invention can measure relative amplitudes of vibration at frequencies between 250 and 20,000 Hz with higher frequencies obtainable. Subsequent measurements on the oval window in human temporal bones in vitro, stimulated with acoustic energy directed into the external auditory canal, further demonstrate the utility of the concept.

It is therefore an object of the present invention to provide for a vibrometer that relies on the detection of motion of the speckle interference pattern produced from the impingement of waves on the surface of a vibrating object.

It is also an object of the present invention to provide for a vibrometer that is not limited to specular reflectance of incident waves, but may also function with diffuse reflectance.

It is an additional object of the present invention to provide for an instrument suitable to measuring the oscillatory motion of vibrating objects, and in particular, the bones, membranes and other structures of the ear.

It is also an object of the present invention to produce an instrument that is significantly less expensive than competing technology, and that is portable and easy to use in vivo.

It is a further object of the present invention to make the instrument able to be used endoscopically thereby allowing the instrument; e.g., to be directed up the Eustachian tube of an ambulatory patient.

Further objects and advantages of the present invention will become apparent from consideration of the detailed description of the preferred embodiments in conjunction with the drawing described as follows.

BRIEF DESCRIPTION OF THE DRAWING

FIG. 1 is a schematic of a laser based embodiment of the vibrometer of the present invention.

FIG. 2 is a perspective detail view of a laser-based, three-dimensional embodiment of the vibrometer of the present invention.

DETAILED DESCRIPTION OF THE PREFERRED EMBODIMENTS

When waves, such as pressure or density waves in matter, or electromagnetic radiation, are reflected off an object whose surface has textural non-uniformities with dimensions on the order of a wavelength of the impinging wave, interference occurs in the reflected beam in the form of a speckle pattern. This effect is particularly pronounced in the case of coherent electromagnetic radiation, such as laser radiation, but the effect occurs even with ordinary light or other wave phenomena. When the reflecting object moves, and in particular when it vibrates, the speckle pattern moves in response. Thus, by monitoring the speckle pattern resulting from reflection off an object having a reflective surface, we are able to monitor the vibrational characteristics of the object. In one embodiment, small bones are the object of interest.

It is an important aspect of the present invention that either diffuse or specular reflectance may be used in the practice of the invention. The preferred embodiments of the invention described below are based upon the use of light, but the present invention is not limited to light and may be employed for measuring the vibrational characteristics of diverse objects using any type of wave phenomena.

We have utilized this principle and developed an instrument (referred to herein as a vibrometer) for the purpose of measuring the vibrational characteristics of objects, and in particular, components of the outer, middle, and inner ear as well as prostheses. While absolute measurements of physical displacement may be difficult with this instrument (requiring calibration), this device is far less expensive than competing technology for simply monitoring the relative magnitude and frequency of vibrations.

A diagram of the preferred embodiment of the vibrometer is shown in FIG. 1. In the preferred embodiment, a laser 10 is employed as the light source, although the present invention is not so limited. The laser 10 is coupled through coupling optics 11 of conventional type to optical fibers 12

(also conventional) which deliver the laser radiation to the object 13 whose vibration is to be measured (in this example, the footplate/oval window of a human temporal bone). Optical fibers are useful in certain contexts; e.g., where the ability of the optical fiber to direct light around bends and curves is important or for access to small or constrained structures, but optical fibers are not required for all applications of the present invention.

In alternative embodiments, the present invention could be applied to the measurement of vibrations of small objects viewed microscopically or of distant objects viewed telescopically. Furthermore, the means of delivery and collection of incident light radiation is not limited to optical fibers. Various optical collection and delivery systems well known in the art would be suitable. Optical fibers are particularly useful in measuring small objects in confined spaces or where the flexibility of the optical fibers allows viewing of objects not in direct line of sight.

A diagram of an alternative embodiment of the present invention as a three-dimensional vibrometer is shown in FIG. 2. The three-dimensional vibrometer consists of three of the vibrometers shown in FIG. 1, each such vibrometer positioned so that is measures the component of object 13's vibration in one of the three mutual orthogonal directions.

In the preferred embodiment, the non-uniform, textural surface of the object 13 reflects the incident laser radiation as a speckle interference pattern which is transmitted by a second optical fiber 14 through coupling optics 15 to a photodetector 16. In the preferred embodiment, the laser 10 is continuous-wave in intensity, and the photodetector 16 is a phototransistor connected to a wide-bandwidth (>100 kHz) amplifier. Other types of photodetectors; e.g., a photodiode, well known in the art may acceptably be employed in the practice of the present invention.

As the object vibrates, the speckle interference pattern moves. The sweep of the speckle interference pattern across the photodetector 16; e.g., the p-n junction of a phototransistor, carries amplitude and frequency information regarding the vibrating object, which is detected and amplified. An analog-to-digital converter 17 may be used to input the signal to a microcomputer/spectrum analyzer 18 to analyze and display the signal. Analog-to-digital converters and spectrum analyzers of conventional type are well known in the field.

Also with reference to FIG. 1, a prototype incorporating the teachings of the vibrometer of the present invention has been tested by monitoring the vibrational characteristics of a piezoelectric transducer 21 excited by the signal from a function generator 19 feeding an audio amplifier 20. This arrangement may also be used to test the functioning of; e.g., the implanted middle ear prostheses discussed above, by exciting an audio source to vibrate the prostheses under test. In the prototype test, the reflected signal from a small amount of typewriter correction fluid placed on the transducer simulated the diffuse reflectance from a white bone.

The presence of harmonics consistent with the vibrational characteristics of a circular (piezoelectric) membrane was detected. The output of the vibrometer when reflected off the transducer oscillating between 250 and 20,000 Hz produced the fundamental frequency of the source signal. It was also determined that the measured amplitude increased with the piezo-transducer driving voltage.

Application of the present invention to the verification of the efficacy of prosthetic implants uses a similar arrangement to that described above with respect to prototype experiment. An audio signal from a piezo-transducer 21 fed to the auditory canal of the patient produces vibrations of; e.g., the oval window, which may be detected by the apparatus of the present invention. By verifying the response of the prosthesis at varying frequencies, the success of the prosthetic implant can be determined.

Having established the instrumental feasibility, we performed experiments designed to elucidate the operative mechanism of the optical vibrometer. In one experiment, we increased the distance between the phototransistor detector and vibrating piezo-transducer thereby sampling less of the reflected hemisphere of light. This resulted in an improved signal-to-noise ratio (SNR) of about 1000. By reducing the distance between the detector and vibrating piezo-transducer, photons of a more highly scattered nature and random phases were more efficiently captured and a reduced SNR resulted. We hypothesize that while these photons may carry vibrational information, they are randomized with respect to photons from the area of the vibrating piezo-transducer which is located in line with the detector. We conclude that strong collimation is one method of improving the SNR of the optical vibrometer, although other methods would be acceptable, such as phase sensitive detection.

Finally, we tested the ability of the vibrometer to detect the vibration of the oval window when the outer ear canal was subjected to clinically relevant sound pressure levels (SPLs). A harvested human temporal bone was drilled out to allow easy access to the tympanic membrane (TM) and the inner ear side of the oval window 13. We used an audiometer 22 and insert earphone 23 with sound tube to produce 250–8000 Hz pure tones with SPLs of 80–90 dB at the end of the tube, which were used to stimulate the TM. The vibrometer was able to detect vibrations in the oval window 13 at each frequency and SPL. Speech, estimated to be 60 dB SPL, was directed into the external ear. The vibrometer was able to detect the resulting vibrations of the oval window 13 and, when the signal was amplified and used to drive audio headphones, speech could be discriminated.

It has been determined that a 10–20 mW diode laser emitting at 690 nm is suitable for the practice of the present invention. Since the laser energy emitted by this laser is relatively low intensity (and thus is a Class II device), it is safe unless directed at the retina for several seconds. Such a laser would nevertheless, require proper labeling and in service training for the end user. With improved instrumentation optics, efficient optical fibers and a sensitive detector, an embodiment of the invention using a lower powered laser could reduce the size of the required power supply and make the radiant energy completely harmless.

While certain preferred embodiments have been described with respect to the use of coherent light to measure the vibrational characteristics of temporal bones, the present invention is directly broadly to the detection of the vibrational characteristics of any object based on the movement of the reflected speckle interference pattern produced by the impingement of waves onto the surface of the object.

The present invention has been described with respect to certain preferred and alternative embodiments which are considered to be exemplary only and not limiting to the full scope of the present invention as set forth in the appended claims.

What is claimed is:

1. A vibrometer, comprising:

a wave source for generating a wave beam for impinging upon a vibrating object having a reflective, irregular surface, said reflective surface of said object having surface irregularities, wherein said wave beam is reflected from said reflective surface as a reflected wave beam comprising a speckle interference pattern;

means for delivering said wave beam to said object;

a detector for generating an electrical output proportional to movement of the speckle interference pattern, said detector comprising a reception surface area that is small relative to the size of speckles in the speckle interference pattern;

means for intercepting said reflected wave beam from said object and delivering said reflected wave beam to said detector.

2. The vibrometer of claim 1 wherein said wave beam is a beam of electromagnetic radiation.

3. The vibrometer of claim 2 wherein said wave source comprises a light source for generating a light beam for irradiating said object;

and wherein said means for delivering said wave beam to said object comprises means for delivering said light beam to said object;

and wherein said detector comprises a photodetector;

and wherein said means for intercepting said reflected wave beam and delivering said reflected wave beam comprises means for intercepting said reflected light beam from said object and delivering said reflected light beam to said photodetector.

4. The vibrometer of claim 3 wherein said means for delivering said light beam to said object comprises fiber optic means.

5. The vibrometer of claim 4 wherein said means for delivering said light beam to said object further comprises coupling optics between said means for delivering said light beam and said light source.

6. The vibrometer of claim 5 wherein said means for intercepting said reflected light beam from said object and delivering said reflected light beam comprises fiber optic means.

7. The vibrometer of claim 6 further comprising an optical bandpass filter between said means for intercepting said reflected light beam and said photodetector.

8. The vibrometer of claim 7 further comprising an amplifier for amplifying said electrical output of said photodetector means.

9. The vibrometer of claim 8 wherein said photodetector means is a photodiode.

10. The vibrometer of claim 8 wherein said photodetector means is a phototransistor.

11. The vibrometer of claim 3 wherein said light source comprises a laser light source.

12. The vibrometer of claim 11 wherein said means for delivering said light beam to said object comprises fiber optic means.

13. The vibrometer of claim 12 wherein said means for delivering said light beam to said object further comprises coupling optics between said means for delivering said light beam and said light source.

14. The vibrometer of claim 13 wherein said means for intercepting said reflected light beam from said object and delivering said reflected light beam comprises fiber optic means.

15. The vibrometer of claim 14 further comprising an optical bandpass filter between said means for intercepting said reflected light beam and said photodetector.

16. The vibrometer of claim 15 further comprising an amplifier for amplifying said electrical output of said photodetector means.

17. The vibrometer of claim 11 wherein said laser light source comprises a laser diode.

18. The vibrometer of claim 11 wherein said laser light source comprises a gas laser.

19. The vibrometer of claim 11 wherein said photodetector means is a photodiode.

20. The vibrometer of claim 11 wherein said photodetector means is a phototransistor.

21. The vibrometer of claim 1 wherein said wave beam is an acoustic beam.

22. A three dimensional vibrometer comprising:

three light sources for generating light beams for irradiating a vibrating object having a reflective surface, said reflective surface of said object having surface irregularities, wherein said light beams are reflected from said reflective surface as reflected light beams comprising a speckle interference pattern;

means for delivering said light beams to said object in mutually orthogonal directions;

three photodetectors for generating an electrical output proportional to movement of the speckle interference pattern, said photodetectors each comprising a reception surface area that is small relative to the size of speckles in the speckle interference pattern;

means for intercepting said reflected light beams from said object and delivering said reflected light beams to said photodetectors.

23. The three dimensional vibrometer of claim 22 wherein said light source comprises a laser light source.

24. The three dimensional vibrometer of claim 23 wherein said laser light source comprises a gas laser.

25. The three dimensional vibrometer of claim 23 wherein said laser light source comprises a laser diode.

26. A method for measuring an object's vibrations on a surface of said object, comprising the steps of:

impinging a wave beam onto the surface of the object to produce a reflected beam comprising a moving speckle interference pattern;

collecting said reflected beam and directing said reflected beam to a detector;

detecting the movement of the speckle interference pattern using a detector comprising a reception surface area that is small relative to the size of speckles in the speckle interference pattern; and extracting vibration information from the detected movement of the speckle interference pattern.

* * * * *